(12) United States Patent
Gooch et al.

(10) Patent No.: US 11,617,544 B2
(45) Date of Patent: Apr. 4, 2023

(54) MEDICAL DEVICES AND METHODS THEREOF FOR DETERMINING BACTERIAL INFECTIONS IN BLOOD

(71) Applicant: Bard Peripheral Vascular, Inc., Franklin Lakes, NJ (US)

(72) Inventors: Nathan Gooch, Centerville, UT (US); Amy Ho, Chandler, AZ (US); Chad K. Nielson, Midvale, UT (US); Scott W. Sanders, Lehi, UT (US); Michelle Passage, Park City, UT (US); Jeff V. Peterson, Mesa, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 0 days.

(21) Appl. No.: 17/763,163

(22) PCT Filed: Sep. 27, 2019

(86) PCT No.: PCT/US2019/053560
§ 371 (c)(1),
(2) Date: Mar. 23, 2022

(87) PCT Pub. No.: WO2021/061156
PCT Pub. Date: Apr. 1, 2021

(65) Prior Publication Data
US 2022/0361821 A1 Nov. 17, 2022

(51) Int. Cl.
*A61B 5/00* (2006.01)
*A61M 1/36* (2006.01)
(Continued)

(52) U.S. Cl.
CPC ........ *A61B 5/6866* (2013.01); *A61B 5/14546* (2013.01); *A61B 5/14735* (2013.01);
(Continued)

(58) Field of Classification Search
CPC .............. A61B 5/6866; A61B 5/14546; A61B 5/14735; A61M 1/3661; A61M 2205/0238; A61M 1/3621; G01N 2800/26
See application file for complete search history.

(56) References Cited

U.S. PATENT DOCUMENTS

| 8,088,060 B2 | 1/2012 | Cottone, Jr. et al. |
| 9,522,217 B2 | 12/2016 | Kutryk et al. |
| 2013/0330747 A1 | 12/2013 | Malima et al. |

FOREIGN PATENT DOCUMENTS

| CN | 107267465 A | 10/2017 |
| DE | 3523615 A1 | 1/1987 |

(Continued)

OTHER PUBLICATIONS

PCT/ US2019/053560 filed Sep. 27, 2019 International Search Report and Written Opinion dated Aug. 12, 2020.

*Primary Examiner* — Leslie R Deak
(74) *Attorney, Agent, or Firm* — Rutan & Tucker LLP (57) ABSTRACT

Medical devices and methods thereof for determining bacterial infections in blood. The medical devices and methods thereof can utilize a coating including an antibody conjugated to a reporter protein configured to indicate a bacterial infection in a patient's blood by way of an antigen thereof. Exemplary medical devices include, but are not limited to, a catheter assembly, an AV fistula needle set, an extension set for either a catheter assembly or an AV fistula needle set, and a hemodialysis tubing set. The medical devices and methods thereof can utilize immunochromatographic separation of the antibody and an antigen-antibody complex to indicate a bacterial infection in a patient's blood.

37 Claims, 6 Drawing Sheets

(51) Int. Cl.
      *A61B 5/145*       (2006.01)
      *A61B 5/1473*     (2006.01)
      *G01N 33/74*      (2006.01)
      *A61B 5/15*        (2006.01)

(52) U.S. Cl.
      CPC ........... *A61M 1/3661* (2014.02); *G01N 33/74* (2013.01); *A61B 5/150992* (2013.01); *G01N 2333/585* (2013.01); *G01N 2800/26* (2013.01)

(56) References Cited

FOREIGN PATENT DOCUMENTS

| | | |
|---|---|---|
| WO | 2016022796 A1 | 2/2016 |
| WO | 2021061156 A1 | 4/2021 |

$$R_{f(a)} = \frac{d_a}{d_s} \qquad R_{f(b)} = \frac{d_b}{d_s} \qquad R_{f(b)} < R_{f(a)}$$

MEDICAL DEVICES AND METHODS THEREOF FOR DETERMINING BACTERIAL INFECTIONS IN BLOOD

PRIORITY

This application is a U.S. national stage application of International Application No. PCT/US2019/053560, filed Sep. 27, 2019, which is incorporated by reference in its entirety into this application.

BACKGROUND

Approximately 50 patients die in the United States every day due to central line-associated bloodstream infections ("CLABSIs"). Even for those patients that survive CLABSIs, CLABSIs cost about $45,000 per infection. In addition, CLABSIs are associated with increased usage of broad-spectrum antibiotics due to a minimum 6-day lead time for obtaining blood-culture results. Overuse of broad-spectrum antibiotics is known to lead to antimicrobial resistance, which, in turn, makes infections such as CLABSIs more difficult to treat. Therefore, the current paradigm of reacting to CLABSIs only after they are mature is not only incurring a high financial cost but also a high cost of mortality and antibiotic burden.

Disclosed herein are medical devices and methods thereof for determining bacterial infections in a blood.

SUMMARY

Disclosed herein is an extension set for a catheter assembly including, in some embodiments, an arterial line and a venous line. The arterial line includes a first length of tubing, a first connector coupled to a distal-end portion of the first length of tubing, and a second connector coupled to a proximal-end portion of the first length of tubing. The first length of tubing has an arterial lumen coated with a coating configured to indicate when an antibody of the coating binds an antigen indicative of a bacterial infection in a patient's blood. The venous line includes a second length of tubing having a venous lumen without the coating, a third connector coupled to a distal-end portion of the second length of tubing, and a fourth connector coupled to a proximal-end portion of the second length of tubing.

In some embodiments, the antibody is conjugated to a reporter protein configured to undergo a conformational change when the antibody binds the antigen.

In some embodiments, the reporter protein is configured to indicate the conformational change by way of a change in color.

In some embodiments, the reporter protein is a reflectin protein.

In some embodiments, the reporter protein is configured to indicate the conformational change by way of a change in fluorescent emission peak.

In some embodiments, the reporter protein is a fluorescent protein.

In some embodiments, the antigen is procalcitonin ("PCT") and the antibody is an anti-PCT antibody.

In some embodiments, at least the first length of tubing is clear and colorless.

In some embodiments, the first and third connectors are Luer connectors.

In some embodiments, the second and fourth connectors are 3-way stopcocks with Luer connectors.

Also disclosed herein is a catheter assembly including, in some embodiments, a hub, a catheter tube coupled to the hub, at least a pair of extension legs coupled to the hub, and a coating thereof configured to indicate when an antibody of the coating binds an antigen indicative of a bacterial infection in a patient's blood. The hub includes at least a pair of hub lumens. The hub lumens form a hub portion of a pair of fluid pathways through the catheter assembly including an arterial lumen and a venous lumen. The catheter tube includes at least a pair of catheter-tube lumens forming a catheter-tube portion of the fluid pathways. Each extension leg of the extension legs includes an extension-leg lumen forming an extension-leg portion of the fluid pathways. The coating is on the arterial lumen of the fluid pathways.

In some embodiments, the antibody is conjugated to a reporter protein configured to undergo a conformational change when the antibody binds the antigen.

In some embodiments, the reporter protein is configured to indicate the conformational change by way of a change in color.

In some embodiments, the reporter protein is a reflectin protein.

In some embodiments, the reporter protein is configured to indicate the conformational change by way of a change in fluorescent emission peak.

In some embodiments, the reporter protein is a fluorescent protein.

In some embodiments, the antigen is PCT and the antibody is an anti-PCT antibody.

In some embodiments, the coating on the arterial lumen is limited to the extension-leg lumen.

In some embodiments, each extension leg of the extension legs includes clear and colorless tubing.

Also disclosed herein is an arteriovenous ("AV") fistula needle set including, in some embodiments, an arterial line and a venous line. The arterial line includes a first length of tubing, a first needle hub coupled to a distal-end portion of the first length of tubing, and a first connector coupled to a proximal-end portion of the first length of tubing. The first length of tubing has an arterial lumen coated with a coating configured to indicate when an antibody of the coating binds an antigen indicative of a bacterial infection in a patient's blood. The first needle hub includes a first needle extending therefrom. The venous line includes a second length of tubing, a second needle hub coupled to a distal-end portion of the second length of tubing, and a second connector coupled to a proximal-end portion of the second length of tubing. The second length of tubing has a venous lumen without the coating. The second needle hub includes a second needle extending therefrom.

In some embodiments, the antibody is conjugated to a reporter protein configured to undergo a conformational change when the antibody binds the antigen.

In some embodiments, the reporter protein is configured to indicate the conformational change by way of a change in color.

In some embodiments, the reporter protein is a reflectin protein.

In some embodiments, the reporter protein is configured to indicate the conformational change by way of a change in fluorescent emission peak.

In some embodiments, the reporter protein is a fluorescent protein.

In some embodiments, the antigen is PCT and the antibody is an anti-PCT antibody.

In some embodiments, at least the first length of tubing is clear and colorless.

In some embodiments, the first and second connectors are Luer connectors.

Also disclosed herein is a hemodialysis tubing set including, in some embodiments, an arterial line and a venous line. The arterial line includes a first plurality of lengths of tubing coupled together by a first plurality of connectors. Each length of tubing of the first plurality of lengths of tubing has an arterial lumen. The arterial lumen of at least one length of tubing of the first plurality of lengths of tubing is coated with a coating configured to indicate when an antibody of the coating binds an antigen indicative of a bacterial infection in a patient's blood. The venous line includes a second plurality of lengths of tubing coupled together by a second plurality of connectors. Each length of tubing of the second plurality of lengths of tubing has a venous lumen without the coating.

In some embodiments, the antibody is conjugated to a reporter protein configured to undergo a conformational change when the antibody binds the antigen.

In some embodiments, the reporter protein is configured to indicate the conformational change by way of a change in color.

In some embodiments, the reporter protein is a reflectin protein.

In some embodiments, the reporter protein is configured to indicate the conformational change by way of a change in fluorescent emission peak.

In some embodiments, the reporter protein is a fluorescent protein.

In some embodiments, the antigen is PCT and the antibody is an anti-PCT antibody.

In some embodiments, at least the one length of tubing coated with the coating is clear and colorless.

In some embodiments, the one length of tubing coated with the coating is between a terminal connector coupled to a distal-end portion of the arterial line and a proximally succeeding internal connector including a port.

Also disclosed herein is a medical device for immunochromatographic determination of a bacterial infection in a patient's blood. The medical device includes, in some embodiments, an absorbent test strip. The absorbent test strip includes an initial band at an origin of the absorbent test strip. The initial band includes an antibody configured to bind an antigen indicative of the bacterial infection in the patient's blood.

In some embodiments, the antibody is conjugated to a dye for visualization.

In some embodiments, the antibody is conjugated to a molecule having a fluorophore for visualization.

In some embodiments, the initial band remains a single band subsequent to developing the absorbent test strip if the antigen is not present in the patient's blood. The absorbent test strip is configured to be developed by capillary action of the patient's blood in a direction away from the origin.

In some embodiments, the initial band separates into two bands having different retention factors subsequent to developing the absorbent test strip if the antigen is present in the patient's blood. The absorbent test strip is configured to be developed by capillary action of the patient's blood in a direction away from the origin. The two bands have different retention factors due to the antibody binding the antigen in one band of the two bands.

In some embodiments, the antigen is PCT and the antibody is an anti-PCT antibody.

Also disclosed herein is a medical device for immunochromatographic determination of a bacterial infection in a patient's blood. The medical device includes, in some embodiments, a barrel, a plunger removably disposed in the barrel, a sidecar coupled to the barrel, and an absorbent test strip disposed in the sidecar. The barrel includes a barrel hub at a barrel hub-end of the barrel and a barrel flange at a barrel flange-end of the barrel. The sidecar is fluidly coupled to the barrel between the barrel hub-end and the barrel flange-end of the barrel. The absorbent test strip includes an initial band at an origin of the absorbent test strip adjacent the barrel. The initial band includes an antibody configured to bind an antigen indicative of the bacterial infection in the patient's blood.

In some embodiments, the antibody is conjugated to a dye for visualization.

In some embodiments, the antibody is conjugated to a molecule having a fluorophore for visualization.

In some embodiments, the initial band remains a single band subsequent to developing the absorbent test strip if the antigen is not present in the patient's blood. The absorbent test strip is configured to be developed by capillary action of the patient's blood in a direction away from the origin.

In some embodiments, the initial band separates into two bands having different retention factors subsequent to developing the absorbent test strip if the antigen is present in the patient's blood. The absorbent test strip is configured to be developed by capillary action of the patient's blood in a direction away from the origin. The two bands have different retention factors due to the antibody binding the antigen in one band of the two bands.

In some embodiments, the antigen is PCT and the antibody is an anti-PCT antibody.

Also disclosed herein is a method of an extension set for a catheter assembly including, in some embodiments, an obtaining step of obtaining the extension set. The extension set includes an arterial line and a venous line. The method also includes a first connecting step of connecting a first connector coupled to a distal-end portion of a first length of tubing of the arterial line to a first extension-leg connector corresponding to an arterial line of a catheter assembly. The first length of tubing has an arterial lumen coated with a coating configured to indicate when an antibody of the coating binds an antigen indicative of a bacterial infection in a patient's blood. The method also includes a second connecting step of connecting a second connector coupled to a proximal-end portion of the first length of tubing to a first terminal connector corresponding to an arterial line of a hemodialysis tubing set. The method also includes an initiating step of initiating hemodialysis with a dialysis system. The method also includes a viewing step of viewing the coating of the arterial lumen through a sidewall of the first length of tubing. The method also includes a determining step of determining if the coating indicates the patient has the bacterial infection.

In some embodiments, the method further includes a third connecting step of connecting a third connector coupled to a distal-end portion of a second length of tubing of the venous line to a second extension-leg connector corresponding to a venous line of the catheter assembly. The second length of tubing does not have the coating. The method also includes a fourth connecting step of connecting a fourth connector coupled to a proximal-end portion of the second length of tubing to a second terminal connector corresponding to a venous line of the hemodialysis tubing set, which completes a blood circuit.

In some embodiments, the determining step includes determining if the coating changes to an expected color resulting from a conformational change in a reflectin protein to which the antibody is conjugated.

In some embodiments, the determining step includes determining if the coating changes to an expected fluorescent emission peak resulting from a conformational change in a fluorescent protein to which the antibody is conjugated.

In some embodiments, the antigen is PCT and the antibody is an anti-PCT antibody.

Also disclosed herein is a method of a catheter assembly including, in some embodiments, an obtaining step of obtaining the catheter assembly. The catheter assembly includes a hub including at least a pair of hub lumens forming a hub portion of a pair of fluid pathways through the catheter assembly. The fluid pathways include an arterial lumen and a venous lumen. The method also includes an inserting step of inserting a catheter tube of the catheter assembly into a central vein of a patient. The catheter tube includes at least a pair of catheter-tube lumens forming a catheter-tube portion of the fluid pathways. The method also includes a first connecting step of connecting a first extension-leg connector coupled to a first extension leg of at least a pair of extension legs of the catheter assembly to a first terminal connector corresponding to an arterial line of a hemodialysis tubing set. Each extension leg of the extension legs includes an extension-leg lumen forming an extension-leg portion of the fluid pathways. The method also includes an initiating step of initiating hemodialysis with a dialysis system. The method also includes a viewing step of viewing a coating of the arterial lumen through a sidewall of the first extension leg. The coating is configured to indicate when an antibody of the coating binds an antigen indicative of a bacterial infection in blood of the patient. The method also includes a determining step of determining if the coating indicates the patient has the bacterial infection.

In some embodiments, the method further includes a second connecting step of connecting a second extension-leg connector coupled to a second extension leg of the extension legs of the catheter assembly to a second terminal connector corresponding to a venous line of the hemodialysis tubing set, which completes a blood circuit.

In some embodiments, the determining step includes determining if the coating changes to an expected color resulting from a conformational change in a reflectin protein to which the antibody is conjugated.

In some embodiments, the determining step includes determining if the coating changes to an expected fluorescent emission peak resulting from a conformational change in a fluorescent protein to which the antibody is conjugated.

In some embodiments, the antigen is PCT and the antibody is an anti-PCT antibody.

Also disclosed herein is a method of an AV fistula needle set including, in some embodiments, an obtaining step of obtaining the AV fistula needle set. The method also includes a first inserting step of inserting a first needle into a vein or graft of a patient. The first needle extends from a first needle hub coupled to a distal-end portion of a first length of tubing having an arterial lumen. The method also includes a first connecting step of connecting a first connector coupled to a proximal-end portion of the first length of tubing to a first terminal connector corresponding to an arterial line of a hemodialysis tubing set. The method also includes an initiating step of initiating hemodialysis with a dialysis system. The method also includes a viewing step of viewing a coating of the arterial lumen through a sidewall of the first length of tubing. The coating is configured to indicate when an antibody of the coating binds an antigen indicative of a bacterial infection in blood of the patient. The method also includes a determining step of determining if the coating indicates the patient has the bacterial infection.

In some embodiments, the method further includes a second inserting step of inserting a second needle into the vein or the graft of the patient. The second needle extends from a second needle hub coupled to a distal-end portion of a second length of tubing having a venous lumen. The method also includes a second connecting step of connecting a second connector coupled to a proximal-end portion of the second length of tubing to a second terminal connector corresponding to a venous line of a hemodialysis tubing set, which completes a blood circuit.

In some embodiments, the determining step includes determining if the coating changes to an expected color resulting from a conformational change in a reflectin protein to which the antibody is conjugated.

In some embodiments, the determining step includes determining if the coating changes to an expected fluorescent emission peak resulting from a conformational change in a fluorescent protein to which the antibody is conjugated.

In some embodiments, the antigen is PCT and the antibody is an anti-PCT antibody.

Also disclosed herein is a method of a hemodialysis tubing set including, in some embodiments, an obtaining step of obtaining the hemodialysis tubing set. The method also includes a first connecting step of connecting an arterial line of the hemodialysis tubing set to a corresponding arterial line of a catheter assembly, an AV fistula needle set, or an extension set between the catheter assembly or the AV fistula needle set by way of a first terminal connector coupled to a first length of tubing of the hemodialysis tubing set. The method also includes an initiating step of initiating hemodialysis with a dialysis system. The method also includes a viewing step of viewing a coating of an arterial lumen through a sidewall of the first length of tubing coated with the coating. The coating is configured to indicate when an antibody of the coating binds an antigen indicative of a bacterial infection in blood of the patient. The method also includes a determining step of determining if the coating indicates the patient has the bacterial infection.

In some embodiments, the method further includes a second connecting step of connecting a venous line of the hemodialysis tubing set to a corresponding venous line of the catheter assembly, the AV fistula needle set, or the extension set by way of a second terminal connector coupled to a second length of tubing of the hemodialysis tubing set, which completes a blood circuit.

In some embodiments, the determining step includes determining if the coating changes to an expected color resulting from a conformational change in a reflectin protein to which the antibody is conjugated.

In some embodiments, the determining step includes determining if the coating changes to an expected fluorescent emission peak resulting from a conformational change in a fluorescent protein to which the antibody is conjugated.

In some embodiments, the antigen is PCT and the antibody is an anti-PCT antibody.

Also disclosed herein is a method of a medical device for immunochromatographic determination of a bacterial infection in a patient's blood. The method includes, in some embodiments, an exposing step of exposing an absorbent test strip to the patient's blood. The absorbent test strip includes an initial band at an origin of the absorbent test strip including an antibody configured to bind an antigen indicative of the bacterial infection in the patient's blood when the antigen is present. The method also includes a developing step of developing the absorbent test strip with the patient's blood by capillary action away from the origin of the absorbent test strip. The method also includes a determining step of determining if the patient has the bacterial infection.

In some embodiments, the method further includes a drawing step of drawing the patient's blood into a barrel of the medical device by at least partially withdrawing a plunger from the barrel to expose the absorbent test strip to the patient's blood. The absorbent test strip is disposed in a sidecar fluidly coupled to the barrel.

In some embodiments, the determining step includes determining if the initial band remains a single band or separates into two bands during or subsequent to the developing step. The single band indicates the antigen is not present in the patient's blood, and the two bands indicates the antigen is present in the patient's blood.

In some embodiments, the antibody is conjugated to a dye for visualization.

In some embodiments, the antibody is conjugated to a molecule having a fluorophore for visualization.

In some embodiments, the antigen is PCT and the antibody is an anti-PCT antibody.

These and other features of the concepts provided herein will become more apparent to those of skill in the art in view of the accompanying drawings and following description, which describe particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, the current paradigm of reacting to CLABSIs only after they are mature is not only incurring a high financial cost but also a high cost of mortality and antibiotic burden.

Disclosed herein are medical devices and methods thereof for determining bacterial infections in blood. Some of the medical devices and methods thereof utilize a coating configured to indicate a bacterial infection in a patient's blood. The foregoing medical devices include, but are not limited to, a catheter assembly, an AV fistula needle set, an extension set for either a catheter assembly or an AV fistula needle set, and a hemodialysis tubing set. Some of the medical devices and methods thereof utilize immunochromatography to indicate a bacterial infection in a patient's blood. It should be understood the medical devices and methods thereof are provided herein in particular embodiments in order to describe certain concepts. Such concepts are not limited to the particular embodiments used to describe the concepts. For example, while the coating configured to indicate a bacterial infection in a patient's blood can be utilized in the catheter assembly, the AV fistula needle set, the extension set, or the hemodialysis tubing set described herein, the coating can also be utilized in a test tube.

Catheter Assembly

Figure 1A:
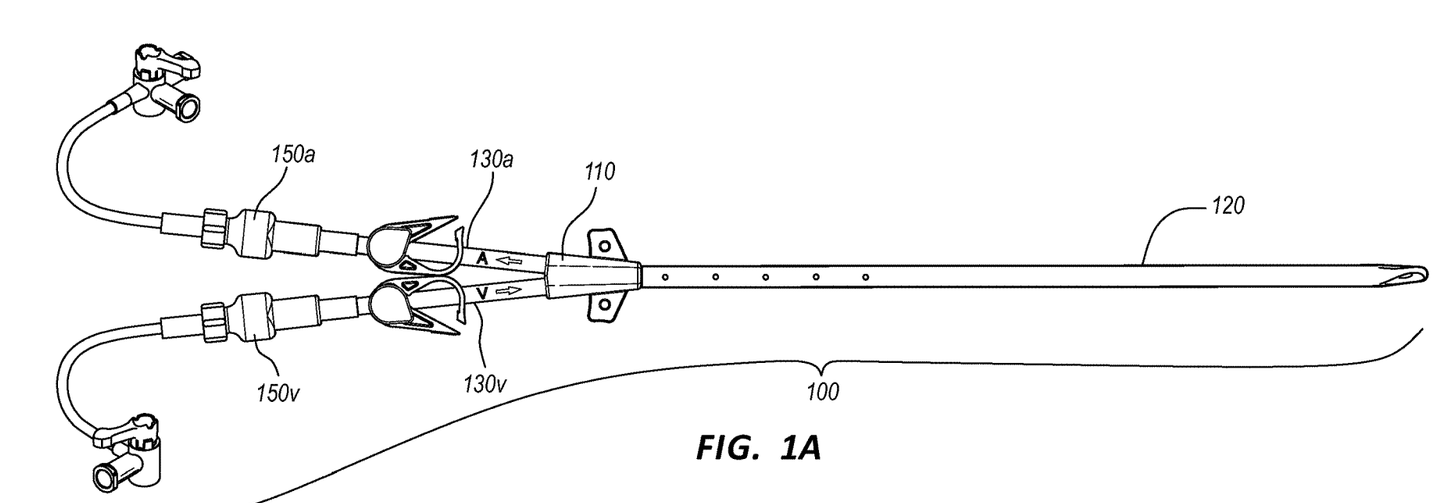
FIG. 1A illustrates a catheter assembly in accordance with some embodiments.
Figure 1B:
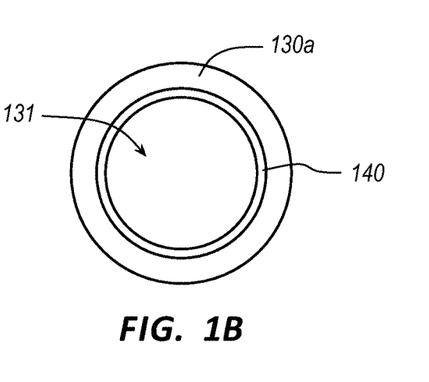
FIG. 1B illustrates a coating of the catheter assembly in accordance with some embodiments.

FIG. 1A illustrates a catheter assembly 100 in accordance with some embodiments. FIG. 1B illustrates a coating 140 of the catheter assembly 100 in accordance with some embodiments.

As shown, the catheter assembly 100 includes a hub 110, a catheter tube 120 coupled to the hub 110, at least a pair of extension legs 130 coupled to the hub 110, and a coating 140 thereof configured to indicate when an antibody of the coating 140 binds an antigen indicative of a bacterial infection in a patient's blood.

While not shown, the hub 110 includes at least a pair of hub lumens. That is, the hub 110 is at least a bifurcated hub for a diluminal catheter. Other embodiments of the catheter assembly include triluminal catheters, tetraluminal catheters, etc., wherein the hub 110 is correspondingly furcated. The hub lumens form a hub portion of a pair of fluid pathways through the catheter assembly 100 including an arterial lumen and a venous lumen.

The catheter tube 120 includes at least a pair of catheter-tube lumens. That is, the catheter-tube lumens match the hub 110 with respect to its furcation. The catheter-tube lumens form a catheter-tube portion of the fluid pathways through the catheter assembly 100.

Each extension leg of the extension legs 130 (e.g., arterial-line extension leg 130a and venous-line extension leg 130v) includes an extension-leg lumen 131 forming an extension-leg portion of the fluid pathways through the catheter assembly 100. Each extension leg of the extension legs 130 includes clear and colorless tubing such that a clinician is able to see through the tubing.

Each extension leg of the extension legs 130 includes an extension-leg connector coupled thereto such as the extension-leg connector 150a or 150v. Such an extension-leg connector can be a male Luer connector coupled to a proximal-end portion of an extension leg.

The coating 140 is on at least the arterial lumen of the fluid pathways through the catheter assembly 100. That said, the coating 140 need not be on the venous lumen of the fluid pathways because only purified blood is expected therethrough when the catheter assembly is used for hemodialysis. In some embodiments, the coating 140 on the arterial lumen of the fluid pathways is limited to the extension-leg lumen 131 or a portion thereof.

Again, the coating 140 is configured to indicate when an antibody of the coating 140 binds an antigen indicative of a bacterial infection in a patient's blood. Such an antibody includes an anti-PCT antibody configured to bind PCT as the antigen.

PCT is a peptide precursor of calcitonin having 116 amino acid residues and a molecular weight of ~13 kDa. PCT is produced by parafollicular cells of the thyroid and neuroendocrine cells of both the lung and the intestine. The average level of PCT in the blood of healthy individuals is very low (<0.05 ng/mL), the PCT having a half-life of about 25 to 30 hours in the blood before being converted to calcitonin.

In response to a bacterial infection, nearly all tissues release PCT into the blood. The level of PCT in the blood can increase to as much as 100 µg/mL as a result of such a bacterial infection making PCT a suitable biomarker thereof. Indeed, clinically relevant levels of PCT in the blood are detectable in just 3 hours after bacterial infection. Due to the relatively short half life of PCT, once the bacterial infection is cleared, the PCT is also quickly cleared from the body.

Anti-PCT antibodies such as ab166963 (Abcam Plc., Cambridge, United Kingdom), 27A3, 6F10, 44d9, or 38F11 (Invitrogen, Carlsbad, Calif.) are suitable as the foregoing anti-PCT antibodies are highly specific for PCT. Indeed, a PCT assay of >0.5 µg/L has been shown to result in a 90% specificity and a 98% sensitivity for bacterial infection.

The antibody (e.g., an anti-PCT antibody) of the coating 140 is conjugated to a reporter protein configured to undergo a conformational change when the antibody binds the antigen (e.g., PCT). The reporter protein can be a reflectin protein, a fluorescent protein, or a modified protein of any of the foregoing. A conjugation kit such as LYNX Rapid Conjugation Kit® or LYNX Rapid Plus Conjugation Kit® (Bio-Rad Laboratories, Inc., Hercules, Calif.) can be used to quickly conjugate the antibody to the reporter protein in at least research settings. At larger scales, one or more conjugation techniques taught in *Bioconjugate Techniques* can be used to conjugate the antibody to the reporter protein. (See Hermanson, Greg T. *Bioconjugate Techniques*. Academic press, 2013.)

Reflectin proteins are configured to indicate the conformational change when the antibody binds the antigen by way of a change in color (e.g., a change to an expected color when the antibody binds the antigen). Indeed, reflectin proteins evolved in certain cephalopods to refract incident light for iridescent camouflage or signaling.

Fluorescent proteins are configured to indicate the conformational change when the antibody binds the antigen by way of a change in fluorescent emission peak (e.g., a change to an expected fluorescent emission peak when the antibody binds the antigen). When the antigen is not bound to a fluorescent protein, the fluorescent protein has a first excitation peak at a particular wavelength and a first emission peak at a particular wavelength. Once the antigen is bound and the reporter protein undergoes the conformational change, the fluorescent protein has a second excitation peak at a particular wavelength and a second emission peak at a particular wavelength. The change in the particular wavelength from the first emission peak to the second emission peak need not be detected because particular wavelength of the second emission peak, itself, indicates the change.

The coating 140 can include the antibody or the reporter protein to which the antibody is conjugated covalently bound to at least the arterial lumen of the fluid pathways through the catheter assembly 100. That is, some portion of the foregoing antibody-reporter protein conjugate can be covalently bound to at least the arterial lumen of the fluid pathways through the catheter assembly 100. Alternatively, the antibody-reporter protein conjugate is part of such as suspended in a pre-coating mixture that is applied to at least the arterial lumen of the fluid pathways through the catheter assembly 100 to form the coating 140 thereon.

A method of the catheter assembly 100 includes an obtaining step of obtaining the catheter assembly 100. The method also includes an inserting step of inserting the catheter tube 120 of the catheter assembly 100 into a central vein of a patient. The method also includes a first connecting step of connecting a first extension-leg connector (e.g., the extension-leg connector 150a) coupled to a first extension leg (e.g., the extension leg 130a) of at least the pair of extension legs 130 of the catheter assembly 100 to a first terminal connector (e.g., the terminal connector 410a of FIG. 4A) corresponding to an arterial line of a hemodialysis tubing set (e.g., the hemodialysis tubing set 410 of FIG. 4A). The method also includes an initiating step of initiating hemodialysis with a dialysis system such as that shown in FIG. 4A. The method also includes a viewing step of viewing a coating (e.g., the coating 140) of an arterial lumen (e.g., the arterial extension-leg lumen 131) through a sidewall of the first extension leg. As set forth above, a coating such as the coating 140 is configured to indicate when an antibody (e.g., an anti-PCT antibody) of the coating 140 binds an antigen (e.g., PCT) indicative of a bacterial infection in blood of the patient. The method also includes a determining step of determining if the coating 140 indicates the patient has the bacterial infection.

In addition to the first connecting step, the method further includes a second connecting step of connecting a second extension-leg connector (e.g., the extension-leg connector 150v) coupled to a second extension leg (e.g., the extension leg 130v) of the extension legs 130 of the catheter assembly 100 to a second terminal connector (e.g., the terminal connector 410v of FIG. 4A) corresponding to a venous line of the hemodialysis tubing set (e.g., the hemodialysis tubing set 410 of FIG. 4A), which completes a blood circuit for the hemodialysis.

With respect to the determining step, the determining step includes determining if the coating 140 changes to an expected color resulting from a conformational change in a reflectin protein to which the antibody is conjugated. Alternatively, the determining step includes determining if the coating 140 changes to an expected fluorescent emission peak resulting from a conformational change in a fluorescent protein to which the antibody is conjugated.

AV Fistula Needle Set

Figures 2A, 2B:
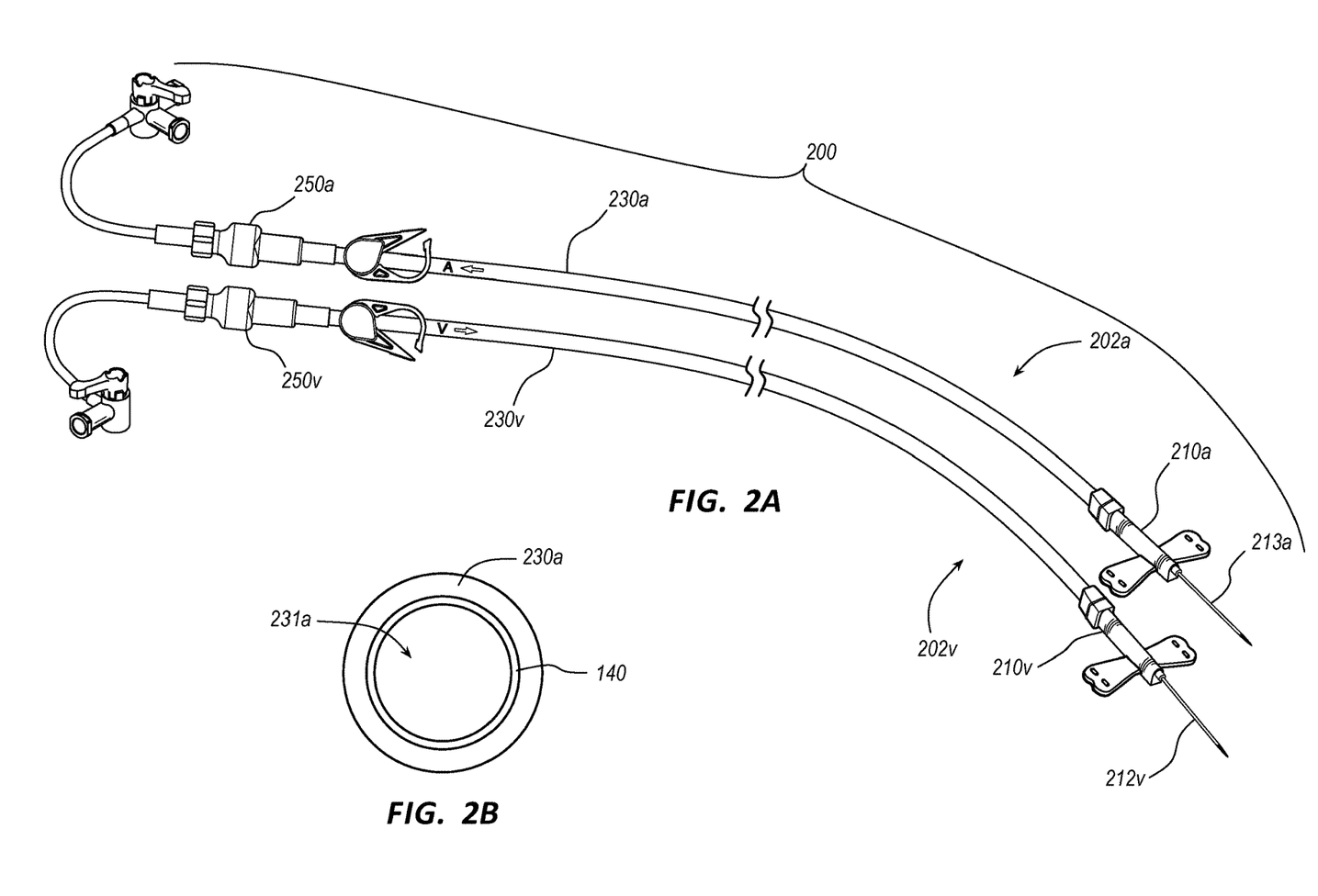
FIG. 2A illustrates an AV fistula needle set in accordance with some embodiments.
FIG. 2B illustrates a coating of the AV fistula needle set in accordance with some embodiments.

FIG. 2A illustrates an AV fistula needle set 200 in accordance with some embodiments. FIG. 2B illustrates the coating 140 of the AV fistula needle set 200 in accordance with some embodiments.

As shown, the AV fistula needle set 200 includes an arterial line 202a and a venous line 202v.

The arterial line 202a includes a needle hub 210a, a length of tubing 230a coupled to the needle hub 210a about a distal-end portion of the length of tubing 230a, and a connector 250a coupled to a proximal-end portion of the length of tubing 230a.

The needle hub 210a includes a needle 212a extending therefrom configured for insertion into a vein or a graft of the patient. The needle hub 210a can have stabilizer wings configured for securing the needle hub 210a to the patient for stabilization of the needle hub 210a. The needle 212a can have a bevel including a back eye for optimum blood flow into the needle 212a.

The length of tubing 230a has an arterial lumen 231a coated with the coating 140 configured to indicate when the antibody of the coating 140 binds the antigen indicative of a bacterial infection in a patient's blood. In some embodiments, the coating 140 is limited to a portion of the length of tubing 230a such as the distal-end portion of the length of tubing 230a or the proximal-end portion of the length of tubing 230a. The length of tubing 230a includes clear and colorless tubing such that a clinician is able to see through the length of tubing 230a.

The connector 250a coupled to the proximal-end portion of the length of tubing 230a can be a male Luer connector.

Likewise, the venous line 202v includes a needle hub 210v having a needle 212v, a length of tubing 230v coupled to the needle hub 210v about a distal-end portion of the length of tubing 230v, and a connector 250v coupled to a proximal-end portion of the length of tubing 230v. The needle hub 210v, the length of tubing 230v, and the connector 250v are as described for the arterial line 202a except the length of tubing 230a has a venous lumen without the coating 140.

As set forth above with respect to the catheter assembly 100, the coating 140 is configured to indicate when an antibody of the coating 140 binds an antigen indicative of a bacterial infection in a patient's blood. Such an antibody includes an anti-PCT antibody configured to bind PCT as the antigen.

The antibody (e.g., an anti-PCT antibody) of the coating 140 is conjugated to a reporter protein configured to undergo a conformational change when the antibody binds the antigen (e.g., PCT). The reporter protein can be a reflectin protein, a fluorescent protein, or a modified protein of any of the foregoing.

A method of the AV fistula needle set 200 includes an obtaining step of obtaining the AV fistula needle set 200. The method also includes a first inserting step of inserting a first needle (e.g., the needle 212a) coupled to a distal-end portion of a first length of tubing (e.g., the length of tubing 230a) into a vein or graft of a patient. The method also includes a first connecting step of connecting a first connector (e.g., the connector 250a) coupled to a proximal-end portion of the first length of tubing to a first terminal connector (e.g., the terminal connector 410a of FIG. 4A) corresponding to an arterial line of a hemodialysis tubing set (e.g., the hemodialysis tubing set 410 of FIG. 4A). The method also includes an initiating step of initiating hemodialysis with a dialysis system such as that shown in FIG. 4A. The method also includes a viewing step of viewing a coating (e.g., the coating 140) of an arterial lumen (e.g., the arterial lumen 231a) through a sidewall of the first length of tubing. As set forth above, a coating such as the coating 140 is configured to indicate when an antibody (e.g., an anti-PCT antibody) of the coating 140 binds an antigen (e.g., PCT) indicative of a bacterial infection in blood of the patient. The method also includes a determining step of determining if the coating 140 indicates the patient has the bacterial infection.

In addition to the first inserting step, the method further includes a second inserting step of inserting a second needle (e.g., the needle 212v) coupled to a distal-end portion of a second length of tubing (e.g., the length of tubing 230v) into the vein or the graft of the patient. In addition to the first connecting step, the method also includes a second connecting step of connecting a second connector (e.g., the connector 250v) coupled to a proximal-end portion of the second length of tubing to a second terminal connector (e.g., the terminal connector 410v of FIG. 4A) corresponding to a venous line of a hemodialysis tubing set (e.g., the hemodialysis tubing set 410 of FIG. 4A), which completes a blood circuit for the hemodialysis.

With respect to the determining step, the determining step includes determining if the coating 140 changes to an expected color resulting from a conformational change in a reflectin protein to which the antibody is conjugated. Alternatively, the determining step includes determining if the coating 140 changes to an expected fluorescent emission peak resulting from a conformational change in a fluorescent protein to which the antibody is conjugated.

Extension Set

Figure 3A:
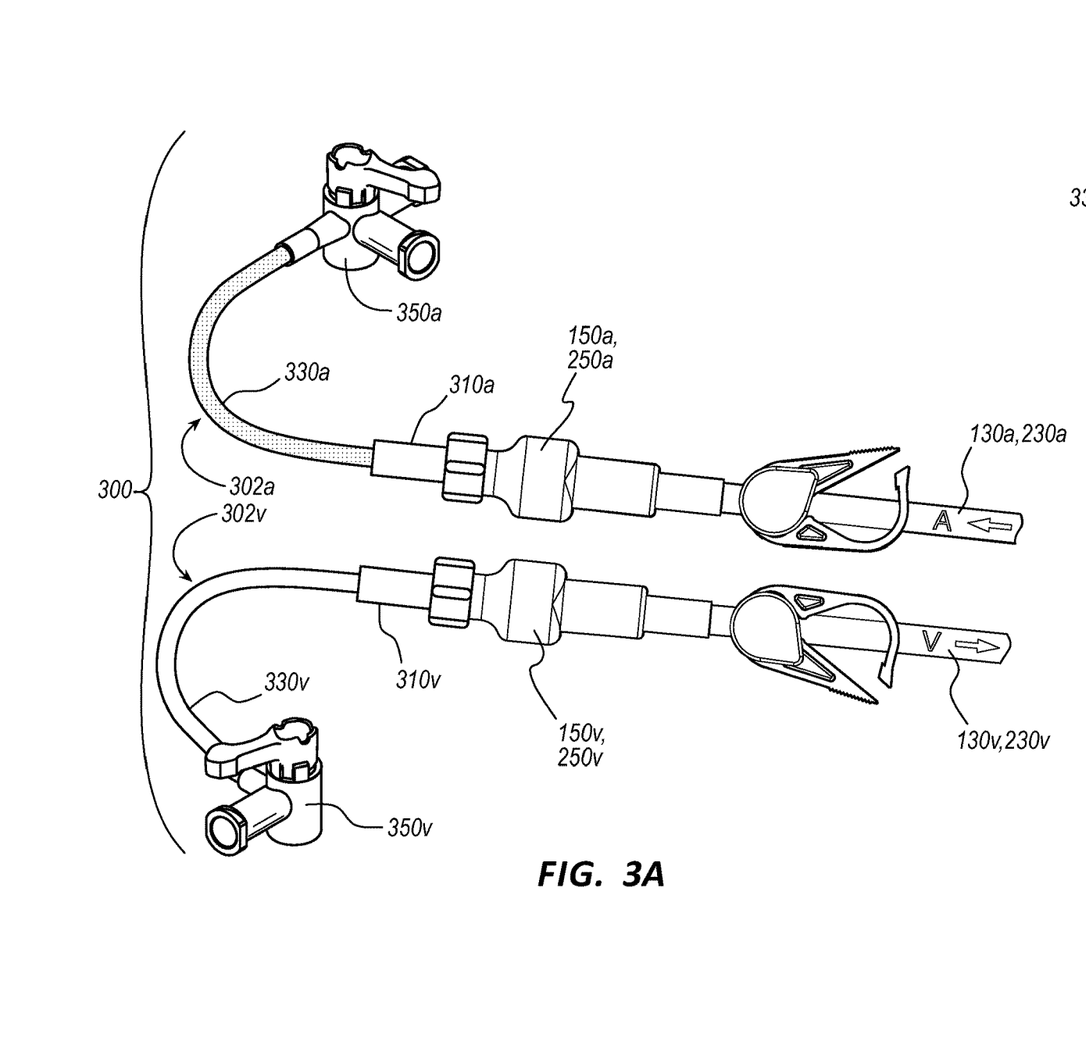
FIG. 3A illustrates an extension set in accordance with some embodiments.
Figure 3B:
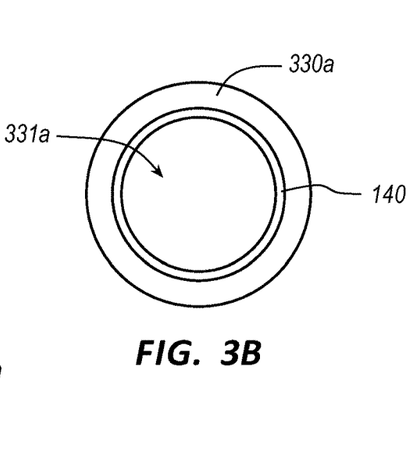
FIG. 3B illustrates a coating of the extension set in accordance with some embodiments.

FIG. 3A illustrates an extension set 300 in accordance with some embodiments. FIG. 3B illustrates the coating 140 of the extension set 300 in accordance with some embodiments.

As shown, the extension set includes an arterial line 302*a* and a venous line 302*v*.

The arterial line 302*a* includes a first connector 310*a*, a length of tubing 330*a* coupled to the first connector 310*a* about a distal-end portion of the length of tubing 330*a*, and a second connector 350*a* coupled to a proximal-end portion of the length of tubing 330*a*.

The length of tubing 330*a* has an arterial lumen 331*a* coated with the coating 140 configured to indicate when the antibody of the coating 140 binds the antigen indicative of a bacterial infection in a patient's blood. In some embodiments, the coating 140 is limited to a portion of the length of tubing 330*a* such as the distal-end portion of the length of tubing 330*a* or the proximal-end portion of the length of tubing 330*a*. The length of tubing 330*a* includes clear and colorless tubing such that a clinician is able to see through the length of tubing 330*a*.

The first connector 310*a* coupled to the distal-end portion of the length of tubing 330*a* can be a female Luer connector. The second connector 350*a* coupled to the proximal-end portion of the length of tubing 330*a* can be a male Luer connector or a 3-way stopcock including a pair of orthogonal male Luer connectors.

Likewise, the venous line 302*v* includes a first connector 310*v*, a length of tubing 330*v* coupled to the first connector 310*v* about a distal-end portion of the length of tubing 330*v*, and a second connector 350*v* coupled to a proximal-end portion of the length of tubing 330*v*. The first connector 310*v*, the length of tubing 230*v*, and the connector 250*v* are as described for the arterial line 302*a* except the length of tubing 330*a* has a venous lumen without the coating 140.

As set forth above with respect to the catheter assembly 100, the coating 140 is configured to indicate when an antibody of the coating 140 binds an antigen indicative of a bacterial infection in a patient's blood. Such an antibody includes an anti-PCT antibody configured to bind PCT as the antigen.

The antibody (e.g., an anti-PCT antibody) of the coating 140 is conjugated to a reporter protein configured to undergo a conformational change when the antibody binds the antigen (e.g., PCT). The reporter protein can be a reflectin protein, a fluorescent protein, or a modified protein of any of the foregoing.

While the extension set 300 can provide an extra bit of length for hemodialysis when needed for a catheter assembly (e.g., the catheter assembly 100 with or without the coating 140) or an AV fistula needle set (e.g., the AV fistula needle set 200 with or without the coating 140), the extension set 300 is configured primarily for determining if a patient has a bacterial infection. With respect to connecting the extension set 300 to either the catheter assembly 100 or the AV fistula needle set 300, connecting such devices in series provides redundancy with respect to determining if a patient has a bacterial infection.

A method of the extension set 300 includes an obtaining step of obtaining the extension set 300. The method also includes a first connecting step of connecting a first connector (e.g., the first connector 310*a*) coupled to a distal-end portion of a first length of tubing (e.g., the length of tubing 330*a*) of an arterial line (e.g., the arterial line 302*a*) to a first extension-leg connector (e.g., the extension-leg connector 150*a*) corresponding to an arterial line of a catheter assembly (e.g., the catheter assembly 100). It should be understood the foregoing catheter assembly need not include the coating 140, but the catheter assembly can be the catheter assembly 100 with the coating 140 for redundancy. The method also includes a second connecting step of connecting a second connector (e.g., the first connector 310*v*) coupled to a proximal-end portion of the first length of tubing to a first terminal connector (e.g., the terminal connector 410*a* of FIG. 4A) corresponding to an arterial line of a hemodialysis tubing set (e.g., the hemodialysis tubing set 410 of FIG. 4A). The method also includes an initiating step of initiating hemodialysis with a dialysis system such as that shown in FIG. 4A. The method also includes a viewing step of viewing a coating (e.g., the coating 140) of an arterial lumen (e.g., the arterial lumen 331*a*) through a sidewall of the first length of tubing. As set forth above, a coating such as the coating 140 is configured to indicate when an antibody (e.g., an anti-PCT antibody) of the coating 140 binds an antigen (e.g., PCT) indicative of a bacterial infection in blood of the patient. The method also includes a determining step of determining if the coating 140 indicates the patient has the bacterial infection.

In addition to the first connecting step, the method further includes a third connecting step of connecting a third connector (e.g., the first connector 310*v*) coupled to a distal-end portion of a second length of tubing (e.g., the length of tubing 330*v*) of a venous line (e.g., the venous line 302*v*) to a second extension-leg connector (e.g., the extension-leg connector 150*v*) corresponding to a venous line of the catheter assembly. In addition to the second connecting step, the method also includes a fourth connecting step of connecting a fourth connector (e.g., the second connector 350*v*) coupled to a proximal-end portion of the second length of tubing to a second terminal connector (e.g., the terminal connector 410*v* of FIG. 4A) corresponding to a venous line of the hemodialysis tubing set (e.g., the hemodialysis tubing set 410 of FIG. 4A), which completes a blood circuit for the hemodialysis.

With respect to the determining step, the determining step includes determining if the coating 140 changes to an expected color resulting from a conformational change in a reflectin protein to which the antibody is conjugated. Alternatively, the determining step includes determining if the coating 140 changes to an expected fluorescent emission peak resulting from a conformational change in a fluorescent protein to which the antibody is conjugated.

While the foregoing method includes connecting the extension set 300 to a catheter assembly such as the catheter assembly 300, the extension set 300 can alternatively be connected in another method to an AV fistula needle set such as the AV fistula needle set 200. For example, instead of the first connecting step of connecting the first connector (e.g., the first connector 310*a*) of the extension set 300 to the first extension-leg connector (e.g., the extension-leg connector 150*a*) of the catheter assembly (e.g., the catheter assembly 100), the first connecting step includes connecting the first connector of the extension set 300 to the first connector (e.g., the connector 250*a*) of the AV fistula needle set (e.g., the AV fistula needle set 200). Likewise, instead of the third connecting step of connecting the third connector (e.g., the first connector 310*v*) of the extension set 300 to the second extension-leg connector (e.g., the extension-leg connector 150*v*) of the catheter assembly (e.g., the catheter assembly 100), the third connecting step includes connecting the third connector of the extension set 300 to the second connector (e.g., the connector 250*v*) of the AV fistula needle set (e.g., the AV fistula needle set 200). Other than the first and third connecting steps, the methods are largely the same. That said, each method of the methods can further include one or more steps (e.g., an inserting step) set forth herein for the catheter assembly 100 or the AV fistula needle set 200 depending upon the method.

Hemodialysis Tubing Set

Figure 4A:
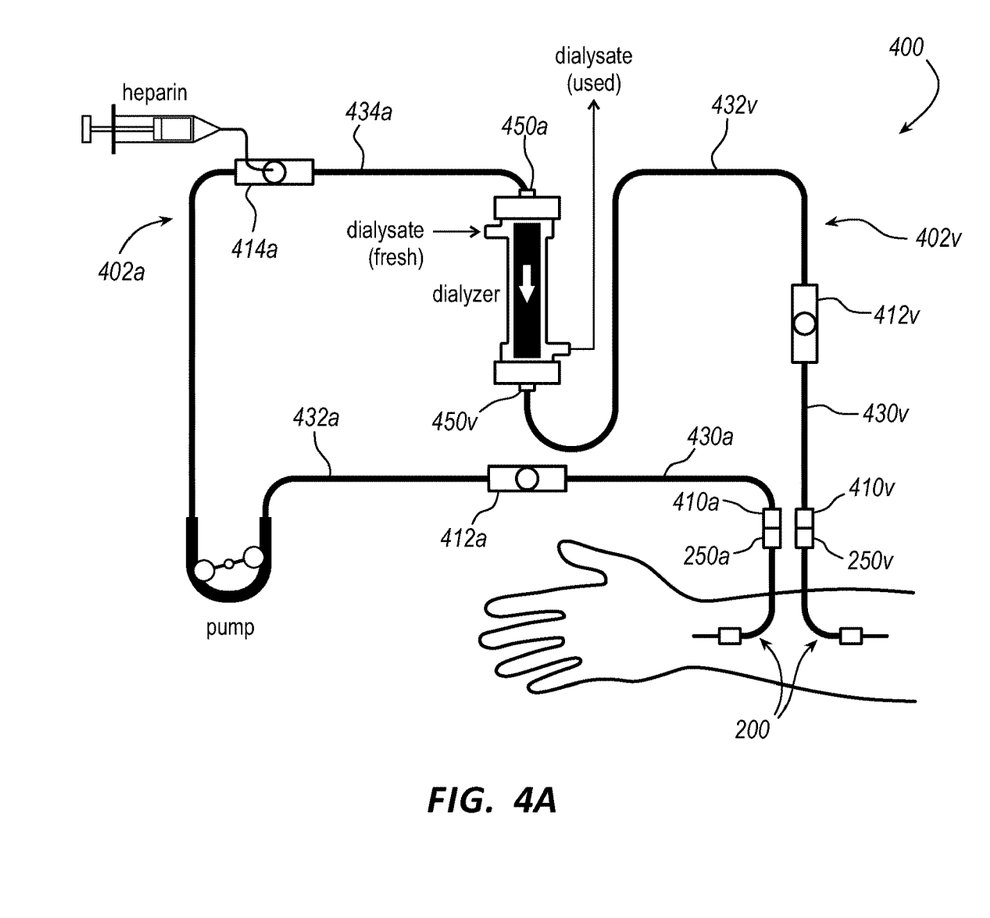
FIG. 4A illustrates a hemodialysis tubing set in a dialysis system in accordance with some embodiments.
Figure 4B:
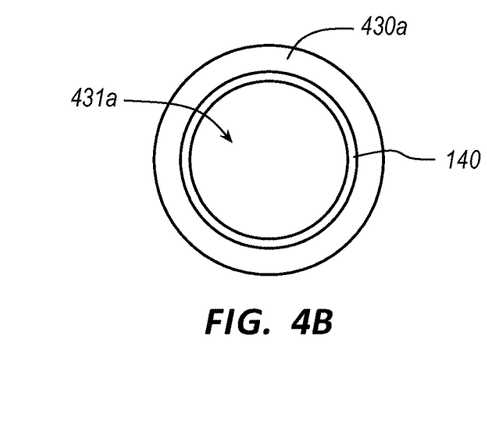
FIG. 4B illustrates a coating of a hemodialysis tubing set in accordance with some embodiments.

FIG. 4A illustrates a hemodialysis tubing set 400 in a dialysis system in accordance with some embodiments. FIG. 4B illustrates the coating 140 of the hemodialysis tubing set 400 in accordance with some embodiments.

As shown, the hemodialysis tubing set 400 includes an arterial line 402*a* and a venous line 402*v*.

The arterial line 402*a* includes a first plurality of lengths of tubing (e.g., a first length of tubing 430*a*, a second length of tubing 432*a*, a third length of tubing 434*a* etc.) coupled together by at least some connectors of a first plurality of connectors (e.g., a terminal connector 410*a*, a first intermediate connector 412*a*, a second intermediate connector 414*a*, a dialyzer connector 450*a*). It should be understood the arterial line 402*a* is an example arterial line of a hemodialysis tubing set. The arterial line 402*a* can include more or fewer lengths of tubing than shown, as well as more or fewer connectors.

Each length of tubing of the first plurality of lengths of tubing has an arterial lumen. For example, the first length of tubing 430*a* has an arterial lumen 431*a*. The arterial lumen of at least one length of tubing of the first plurality of lengths of tubing is coated with the coating 140 configured to indicate when the antibody of the coating binds the antigen indicative of a bacterial infection in a patient's blood. In some embodiments, the coating 140 is limited to the first length of tubing 430*a* between the terminal connector 410*a* coupled to a distal-end portion of the first length of tubing 430*a* and the first intermediate connector 412*a* coupled to a proximal-end portion of the first length of tubing 430*a*. The coating 140 can be further limited to a portion of the first length of tubing 430*a* such as the distal-end portion of the first length of tubing 430*a* or the proximal-end portion of the first length of tubing 430*a*. The at least one length of tubing including the coating 140 includes clear and colorless tubing such that a clinician is able to see therethrough. That said, each length of tubing of the first plurality of lengths of tubing can include clear and colorless tubing.

The terminal connector 410*a* coupled to the distal-end portion of the length of tubing 330*a* can be a female Luer connector. Each intermediate connector of the first intermediate connector 412*a* and the second intermediate connector 414*a* can include a port configured for therapeutic injections. For example, the intermediate connector 414*a* includes a port configured for heparin injections to prevent clotting. The dialyzer connector 450*a* coupled to a proximal-end portion of the length of tubing 434*a* can be a female Luer connector.

Likewise, the venous line 302*v* includes a second plurality of lengths of tubing (e.g., a first length of tubing 430*v*, a second length of tubing 432*v*, etc.) coupled together by at least some connectors of a second plurality of connectors (e.g., a terminal connector 410*v*, a first intermediate connector 412*v*, a dialyzer connector 450*v*). The second plurality of lengths of tubing and the second plurality of connectors are as described for the first plurality of lengths of tubing and the first plurality of connectors of the arterial line 302*a* except the length of tubing 430*v* has a venous lumen without the coating 140.

As set forth above with respect to the catheter assembly 100, the coating 140 is configured to indicate when an antibody of the coating 140 binds an antigen indicative of a bacterial infection in a patient's blood. Such an antibody includes an anti-PCT antibody configured to bind PCT as the antigen.

The antibody (e.g., an anti-PCT antibody) of the coating 140 is conjugated to a reporter protein configured to undergo a conformational change when the antibody binds the antigen (e.g., PCT). The reporter protein can be a reflectin protein, a fluorescent protein, or a modified protein of any of the foregoing.

A method of the hemodialysis tubing set 400 includes an obtaining step of obtaining the hemodialysis tubing set 400. The method also includes a first connecting step of connecting the arterial line 402*a* of the hemodialysis tubing set 400 to a corresponding arterial line of a catheter assembly (e.g., the catheter assembly 100), an AV fistula needle set (e.g., the AV fistula needle set 200), or an extension set (e.g., the extension set 300) between the catheter assembly or the AV fistula needle set by way of the first terminal connector 410*a* of the first plurality of connectors coupled to the first length of tubing 430*a* of the first plurality of lengths of tubing. The method also includes an initiating step of initiating hemodialysis with a dialysis system. The method also includes a viewing step of viewing the coating 140 of the arterial lumen 431*a* through a sidewall of the first length of tubing 430*a* of the first plurality of lengths of tubing. As set forth above, the coating 140 is configured to indicate when an antibody (e.g., an anti-PCT antibody) of the coating 140 binds an antigen (e.g., PCT) indicative of a bacterial infection in blood of the patient. The method also includes a determining step of determining if the coating 140 indicates the patient has the bacterial infection.

In addition to the first connecting step, the method further includes a second connecting step of connecting the venous line 402*v* of the hemodialysis tubing set 400 to a corresponding venous line of the catheter assembly, the AV fistula needle set, or the extension set by way of the first terminal connector 410*v* of the second plurality of connectors coupled to the first length of tubing 430*v* of the second plurality of lengths, which completes a blood circuit for the hemodialysis.

With respect to the determining step, the determining step includes determining if the coating 140 changes to an expected color resulting from a conformational change in a reflectin protein to which the antibody is conjugated. Alternatively, the determining step includes determining if the coating 140 changes to an expected fluorescent emission peak resulting from a conformational change in a fluorescent protein to which the antibody is conjugated.

While the foregoing method includes the arterial lumen 431*a* of the first length of tubing 430*a* of the first plurality of lengths of tubing coated with the coating 140, other lengths of tubing of the first plurality of lengths of tubing can alternatively or additionally include the coating 140 as set forth herein. Consequently, the viewing step of the foregoing method can alternatively or additionally include viewing the coating 140 through a sidewall of the one or more other lengths of the first plurality of lengths of tubing.

All medical device set forth herein above are intended as single-use medical devices to mitigate blood fouling the coating 140.

Immunochromatographic Device

Figure 5A:
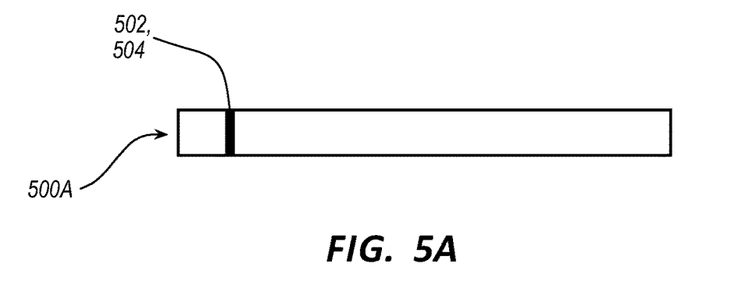
FIG. 5A illustrates an undeveloped adsorbent test strip configured for immunochromatography in accordance with some embodiments.
Figure 5B:
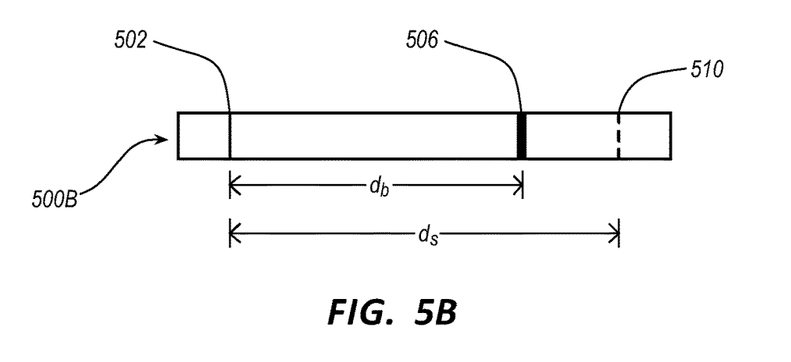
FIG. 5B illustrates a developed adsorbent test strip in accordance with some embodiments.
Figure 5C:
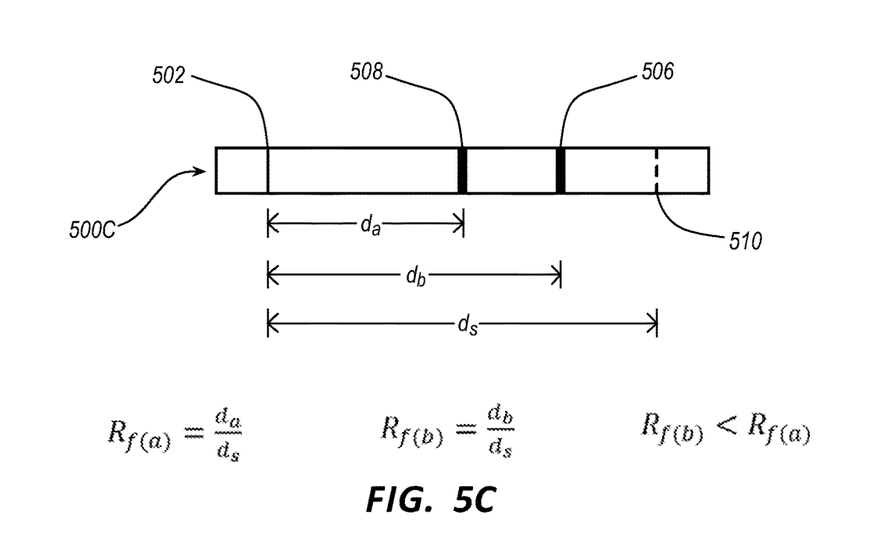
FIG. 5C illustrates another developed adsorbent test strip in accordance with some embodiments.

FIG. 5A illustrates an undeveloped adsorbent test strip 500A configured for immunochromatographic determination of a bacterial infection in a patient's blood in accordance with some embodiments. FIG. 5B illustrates a developed adsorbent test strip 500B in accordance with some embodiments. FIG. 5C illustrates another developed adsorbent test strip 500C in accordance with some embodiments.

As shown, a medical device for the immunochromatographic determination of a bacterial infection in a patient's blood includes the adsorbent test strip 500A.

The absorbent test strip 500A includes an origin 502 and an initial band 504 at the origin 502 of the absorbent test strip 500A. The initial band 504 includes an antibody (e.g., an anti-PCT antibody) configured to bind an antigen (e.g., PCT) indicative of a bacterial infection in a patient's blood.

The antibody (e.g., an anti-PCT antibody) of the initial band 504 is conjugated to a dye or a fluorescent molecule for visualization. A conjugation kit such as LYNX Rapid Conjugation Kit® or LYNX Rapid Plus Conjugation Kit® (Bio-Rad Laboratories, Inc., Hercules, Calif.) can be used to quickly conjugate the antibody to the dye or the fluorescent molecule in at least research settings. At larger scales, one or more conjugation techniques taught in *Bioconjugate Techniques* can be used to conjugate the antibody to the dye or the fluorescent molecule. (See Hermanson, Greg T. *Bioconjugate Techniques*. Academic press, 2013.) Alternatively, the antibody is not conjugated to another molecule. Instead, the absorbent test strip 500A includes an integrated fluorescent indicator (e.g., manganese-doped zinc silicate). A band of the antibody such as the initial band 504 appears dark against the absorbent test strip 500A when fluorescence is induced in the fluorescent indicator by light at or near the peak excitation wavelength of the fluorescent indicator.

The absorbent test strip 500A is configured to be developed by capillary action of the patient's blood in a direction away from the origin 502, which can lead to either the developed absorbent test strip 500B or the developed absorbent test strip 500C depending upon whether a patient's blood includes the antigen to the antibody. The initial band 504 remains a single band—albeit with a non-zero retention factor—subsequent to developing the absorbent test strip 500A if the antigen is not present in the patient's blood. This is shown by a band 506 of the antibody or the antibody conjugated to the dye or fluorescent molecule of the developed absorbent test strip 500B. However, the initial band 504 separates into two bands having different retention factors subsequent to developing the absorbent test strip 500A if the antigen is present in the patient's blood. This is shown by the band 506 and a band 508 of the antigen-antibody complex or the antigen-antibody complex conjugated to the dye or fluorescent molecule of the developed absorbent test strip 500C. Due to the antibody binding the antigen, the retention factor of the band 508 is less than the retention factor of the band 506 as shown in FIG. 5C.

In addition to illustrating the developed absorbent test strip 500C, FIG. 5C also illustrates calculation of a retention factor $R_f$, which is a ratio of a distance travelled by the band 506 or the band 508 to a distance travelled by a solvent as indicated by a solvent front 510.

Figure 6:
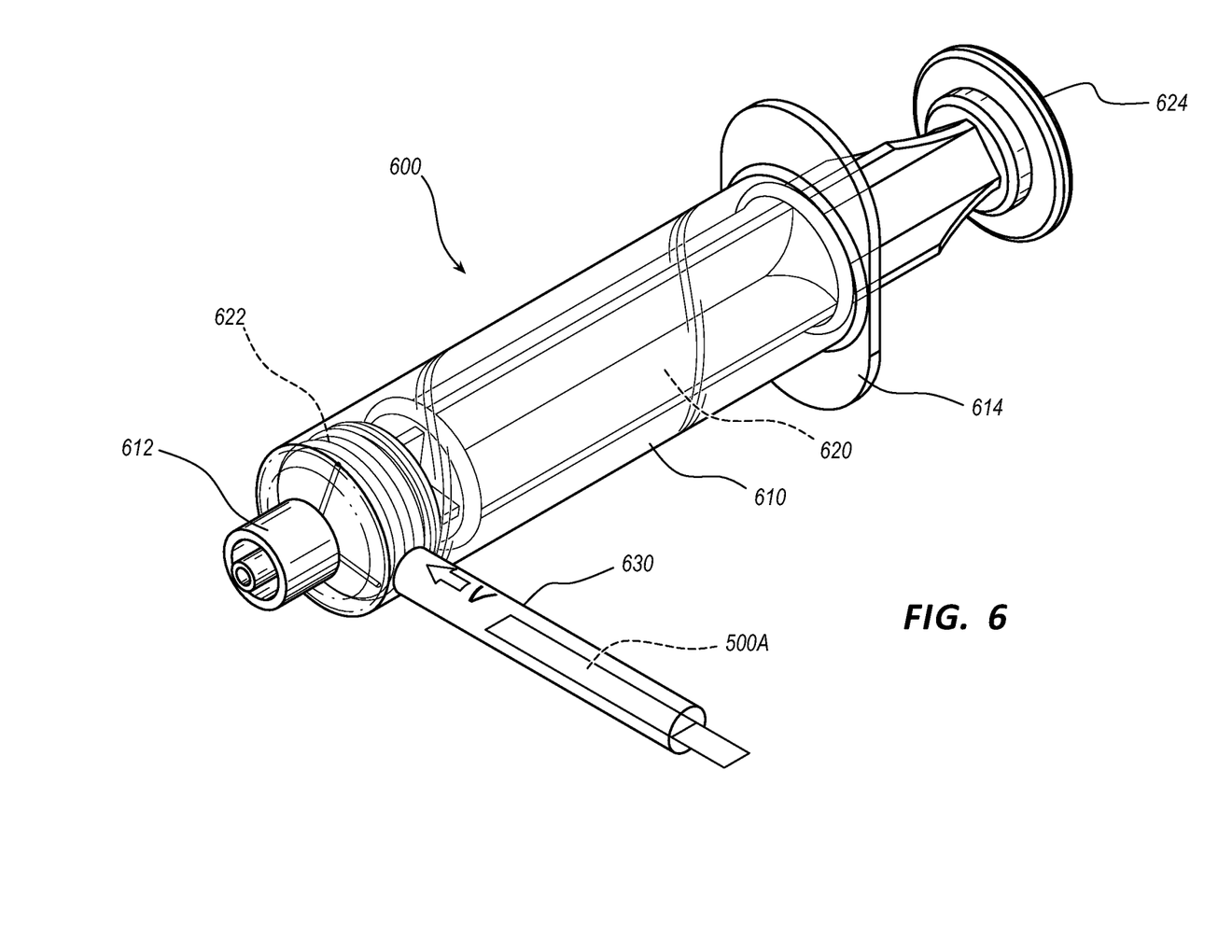
FIG. 6 illustrates a medical device configured for immunochromatography in accordance with some embodiments.

FIG. 6 illustrates a medical device 600 configured for the immunochromatographic determination of a bacterial infection in a patient's blood in accordance with some embodiments.

As shown, the medical device 600 includes a barrel 610, a plunger 620 removably disposed in the barrel 610, a sidecar 630 fluidly coupled to the barrel 610, and the absorbent test strip 500A disposed in the sidecar 630.

The barrel 610 includes a barrel hub 612 at a barrel hub-end of the barrel 610 and a barrel flange 614 at a barrel flange-end of the barrel 610.

The plunger 620 includes a seal 622 at a seal-end of the plunger 620 and a plunger flange 624 at a plunger flange-end of the plunger 620. The seal 622 is configured to seal a patient's blood in the barrel 610 so as to not contaminate the blood or expose a clinician to the blood. A combination of the barrel flange 614 and the plunger flange 624 provides grips configured to facilitate drawing the patient's blood into the barrel 610.

The sidecar 630 is fluidly coupled to the barrel 610 between the barrel hub-end and the barrel flange-end of the barrel 610. Being fluidly coupled to the barrel 610, the sidecar 630 is configured to accept therein a portion of the patient's blood from the barrel 610 for developing the absorbent test strip 500A by capillary action. The portion of the patient's blood from the barrel 610 released to the sidecar 630 is sufficient for developing the absorbent test strip 500A, which is disposed in the sidecar 630 such that a tip of the absorbent test strip 500A at an origin-end of the of the absorbent test strip 500A is adjacent the barrel 610.

As set forth above with respect to the absorbent test strips 500A, 500B, and 500C, the absorbent test strip 500A is configured to be developed by capillary action of a patient's blood in a direction away from the origin 502, which can lead to the developed absorbent test strip 500B or 500C depending upon whether the patient's blood includes the antigen to the antibody in the initial band 504. Again, the developed test strip 500B includes only the band 506, which includes only the antibody or the antibody conjugated to the dye or fluorescent molecule. That is, a presence of only one band (i.e., the band 506) on the developed test strip 500B indicates the antigen is not present and the patient does not have a bacterial infection. However, the developed test strip 500C includes both the band 506 and the band 508, the latter of which includes the antigen-antibody complex or the antigen-antibody complex conjugated to the dye or fluorescent molecule. That is, a presence of both bands (i.e., the band 506 and the band 508) on the developed test strip 500C indicates the antigen is present and the patient does have a bacterial infection.

A method of a medical device such as the absorbent test strip 500A or the medical device 600 includes an exposing step of exposing the absorbent test strip 500A to a patient's blood for immunochromatographic determination of a bacterial infection in the patient's blood. The method also includes a developing step of developing the absorbent test strip 500A with the patient's blood by capillary action away from the origin 502 of the absorbent test strip 500A. The method also includes a determining step of determining if the patient has the bacterial infection.

When the medical device 600 is used, the method further includes a drawing step of drawing the patient's blood into the barrel 610 by at least partially withdrawing the plunger 620 from the barrel 610 to expose the absorbent test strip 500A disposed in the sidecar 630 to the patient's blood.

With respect to the determining step, the determining step includes determining if the initial band 504 remains a single band (e.g., the band 506) or separates into two bands (e.g., the band 506 and the band 508) during or subsequent to the developing step. Again, the single band indicates the antigen is not present in the patient's blood and the patient does not have a bacterial infection. However, the two bands indicates the antigen is present in the patient's blood and the patient has a bacterial infection.

Because a bacterial infection is currently detected by observing a patient already expressing symptoms, and because a minimum 6-day lead time is needed for obtaining blood-culture results to confirm the symptoms are a result of a bacterial infection, visual detection of PCT and, thus, bacterial infection in accordance with the medical devices and methods set forth herein advantageously provides clinicians an opportunity to intervene and address bacterial infections such as the foregoing before the bacterial infections become mature and life threatening. Such early intervention can significantly reduce high financial costs associated with CLABSIs, as well as the high costs of mortality and antibiotic burden associated with CLABSIs.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. An extension set for a catheter assembly, comprising:
   an arterial line including:
      a first length of tubing having an arterial lumen coated with a coating configured to indicate when an antibody of the coating binds an antigen indicative of a bacterial infection in a patient's blood;
      a first connector coupled to a distal-end portion of the first length of tubing; and
      a second connector coupled to a proximal-end portion of the first length of tubing; and
   a venous line including:
      a second length of tubing having a venous lumen without the coating;
      a third connector coupled to a distal-end portion of the second length of tubing; and
      a fourth connector coupled to a proximal-end portion of the second length of tubing.

2. The extension set of claim 1, wherein the antibody is conjugated to a reporter protein configured to undergo a conformational change when the antibody binds the antigen.

3. The extension set of claim 2, wherein the reporter protein is configured to indicate the conformational change by way of a change in color.

4. The extension set of claim 3, wherein the reporter protein is a reflectin protein.

5. The extension set of claim 2, wherein the reporter protein is configured to indicate the conformational change by way of a change in fluorescent emission peak.

6. The extension set of claim 5, wherein the reporter protein is a fluorescent protein.

7. The extension set of claim 1, wherein the antigen is procalcitonin ("PCT") and the antibody is an anti-PCT antibody.

8. The extension set of claim 1, wherein at least the first length of tubing is clear and colorless.

9. The extension set of claim 1, wherein the first and third connectors are Luer connectors.

10. The extension set of claim 1, wherein the second and fourth connectors are 3-way stopcocks with Luer connectors.

11. A catheter assembly, comprising:
    a hub including at least a pair of hub lumens, the hub lumens forming a hub portion of a pair of fluid pathways through the catheter assembly including an arterial lumen and a venous lumen;
    a catheter tube coupled to the hub, the catheter tube including at least a pair of catheter-tube lumens forming a catheter-tube portion of the fluid pathways;
    at least a pair of extension legs coupled to the hub, each extension leg of the extension legs including an extension-leg lumen forming an extension-leg portion of the fluid pathways; and
    a coating on the arterial lumen configured to indicate when an antibody of the coating binds an antigen indicative of a bacterial infection in a patient's blood.

12. The catheter assembly of claim 11, wherein the antibody is conjugated to a reporter protein configured to undergo a conformational change when the antibody binds the antigen.

13. The catheter assembly of claim 12, wherein the reporter protein is configured to indicate the conformational change by way of a change in color.

14. The catheter assembly of claim 13, wherein the reporter protein is a reflectin protein.

15. The catheter assembly of claim 12, wherein the reporter protein is configured to indicate the conformational change by way of a change in fluorescent emission peak.

16. The catheter assembly of claim 15, wherein the reporter protein is a fluorescent protein.

17. The catheter assembly of claim 11, wherein the antigen is procalcitonin ("PCT") and the antibody is an anti-PCT antibody.

18. The catheter assembly of claim 11, wherein the coating on the arterial lumen is limited to the extension-leg lumen.

19. The catheter assembly of claim 11, wherein each extension leg of the extension legs includes clear and colorless tubing.

20. An arteriovenous ("AV") fistula needle set, comprising:
    an arterial line including:
       a first length of tubing having an arterial lumen coated with a coating configured to indicate when an antibody of the coating binds an antigen indicative of a bacterial infection in a patient's blood;
       a first needle hub including a first needle extending therefrom coupled to a distal-end portion of the first length of tubing; and
       a first connector coupled to a proximal-end portion of the first length of tubing; and
    a venous line including:
       a second length of tubing having a venous lumen without the coating;
       a second needle hub including a second needle extending therefrom coupled to a distal-end portion of the second length of tubing; and
       a second connector coupled to a proximal-end portion of the second length of tubing.

21. The AV fistula needle set of claim 20, wherein the antibody is conjugated to a reporter protein configured to undergo a conformational change when the antibody binds the antigen.

22. The AV fistula needle set of claim 21, wherein the reporter protein is configured to indicate the conformational change by way of a change in color.

23. The AV fistula needle set of claim 22, wherein the reporter protein is a reflectin protein.

24. The AV fistula needle set of claim 21, wherein the reporter protein is configured to indicate the conformational change by way of a change in fluorescent emission peak.

25. The AV fistula needle set of claim 24, wherein the reporter protein is a fluorescent protein.

26. The AV fistula needle set of claim 20, wherein the antigen is procalcitonin ("PCT") and the antibody is an anti-PCT antibody.

27. The AV fistula needle set of claim 20, wherein at least the first length of tubing is clear and colorless.

28. The AV fistula needle set of claim 20, wherein the first and second connectors are Luer connectors.

29. A hemodialysis tubing set, comprising:

an arterial line including:

a first plurality of lengths of tubing coupled together by a first plurality of connectors, each length of tubing of the first plurality of lengths of tubing having an arterial lumen;

a coating configured to indicate when an antibody of the coating binds an antigen indicative of a bacterial infection in a patient's blood, the arterial lumen of at least one length of tubing of the first plurality of lengths of tubing coated with the coating; and a venous line including a second plurality of lengths of tubing coupled together by a second plurality of connectors, each length of tubing of the second plurality of lengths of tubing having a venous lumen without the coating.

30. The hemodialysis tubing set of claim 29, wherein the antibody is conjugated to a reporter protein configured to undergo a conformational change when the antibody binds the antigen.

31. The hemodialysis tubing set of claim 30, wherein the reporter protein is configured to indicate the conformational change by way of a change in color.

32. The hemodialysis tubing set of claim 31, wherein the reporter protein is a reflectin protein.

33. The hemodialysis tubing set of claim 30, wherein the reporter protein is configured to indicate the conformational change by way of a change in fluorescent emission peak.

34. The hemodialysis tubing set of claim 33, wherein the reporter protein is a fluorescent protein.

35. The hemodialysis tubing set of claim 29, wherein the antigen is procalcitonin ("PCT") and the antibody is an anti-PCT antibody.

36. The hemodialysis tubing set of claim 29, wherein at least the one length of tubing coated with the coating is clear and colorless.

37. The hemodialysis tubing set of claim 29, wherein the one length of tubing coated with the coating is between a terminal connector coupled to a distal-end portion of the arterial line and a proximally succeeding internal connector including a port.

* * * * *